United States Patent [19]

Warner, Jr.

[11] 3,953,589

[45] Apr. 27, 1976

[54] METHOD FOR PROTECTING HUMAN SKIN FROM ULTRAVIOLET RADIATION

[75] Inventor: Paul L. Warner, Jr., Clarence, N.Y.

[73] Assignee: Westwood Pharmaceuticals, Inc., Buffalo, N.Y.

[22] Filed: Sept. 27, 1974

[21] Appl. No.: 509,997

Related U.S. Application Data

[63] Continuation of Ser. No. 351,398, April 16, 1973, abandoned.

[52] U.S. Cl. .................................. 424/60; 252/300; 260/573; 424/174
[51] Int. Cl.$^2$ .......................................... A61K 7/44
[58] Field of Search ............... 424/59, 60, 330, 331

[56] References Cited
UNITED STATES PATENTS

| | | | |
|---|---|---|---|
| 2,369,084 | 2/1945 | Stockelbach | 424/60 |
| 3,506,758 | 4/1970 | Epstein et al. | 424/60 |

OTHER PUBLICATIONS

Werner *Chem. Abs.*, 1969, Vol. 70, p. 3564.

*Primary Examiner*—Dale R. Ore
*Attorney, Agent, or Firm*—James Magee, Jr.

[57] ABSTRACT

The specification discloses 4-N,N-bis-(2-hydroxyethyl)aminoacylphenones which are useful as sunscreening agents for absorbing intermediate range radiation. The acyl moiety is derived from the group of alkanoic acids having from 2 to about 16 carbon atoms.

7 Claims, No Drawings

METHOD FOR PROTECTING HUMAN SKIN FROM ULTRAVIOLET RADIATION

BACKGROUND OF THE INVENTION

This is a continuation of application Ser. No. 351,398 filed Apr. 16, 1973, now abandoned.

It is well known that electromagnetic radiation which emanates from the sun and passes through the atmosphere of the earth, and which is in the range of 297 nm to 320 nm, may have a detrimental and deleterious effect on paints, plastics, and certain other substances. It is further recognized that electromagnetic radiation is harmful and damaging to human skin since this wavelength range causes cutaneous sunburn and carcinogenesis. This range of radiation is often referred to as the erthromogenic region.

It is not as well known that regions of electromagnetic radiation generally in the range of 320 nm to about 700 nm but more usually in the range of 320 nm to about 450 nm can cause, directly or indirectly, an adverse effect or response to the skin and to subcutaneous tissues and organs, particularly in connection with the influence of other agents, e.g., coal tar extracts, plant extracts, phenothiazines, furocoumarans, and halogenated salicylanilides.

More particularly the influence of sunlight in connection with the use of such drugs by topical, oral, or parenteral administration to the patient can cause adverse effects, for example, edema, hyperpigmentation, vesicle formation, urticaria, and exaggerated sunburn. Other disorders such as polymorphic light eruptions, certain porphyrias, and lupus erythematosis are, apparently, significantly exaggerated by light of these longer wavelengths, i.e., 320 to 360 nm.

The electromagnetic radiation within the ultraviolet and visible spectrum incident to an object can be blocked by a mechanical barrier, e.g., of titanium dioxide, which prevents passage of all radiation regardless of wavelength. Another method which permits the greater part of the incident radiation to pass through and which takes out only a narrow spectrum of such radiation is the employment of a selective sunscreen agent. A sunscreen agent is a chemical substance which interacts photochemically with radiation of certain wavelengths of the electromagnetic spectrum to remove all or part of these wavelengths. Thus important criteria for a sunscreening agent are (1) the ability to absorb light, i.e., to display an ultraviolet or visible light absorption spectrum and (2) to absorb the light efficiently, i.e., to have a molar absorptivity (extinction coefficient) of at least 20,000.

For the purpose of discussion, a short-range sunscreen agent is defined as a substance which absorbs light efficiently in the range of 297 nm to 320 nm. An intermediate-range sunscreen is a substance which absorbs light efficiently in the 320 nm to 360 nm range. A long-range sunscreen is a substance which efficiently absorbs light above 360 nm.

It would be beneficial to have available chemical substances which absorb a relatively narrow-selected range of solor electromagnetic radiation. It would be particularly beneficial to have substances which absorb beyond the erythromogenic range.

Para-aminobenzoic acid and certain esters thereof are compounds which absorb light efficiently in the erythromogenic regions and are popularly employed to prevent sunburn. These compounds are readily available in commercial sunscreening formulations. Certain benzophenones, which generally have lower molar extinction coefficients but a wide range of spectral absorption, are also available in commercial formulations as sunburn preventatives. There appears to be no chemical substances which are employed solely as intermediate-range sunscreens for those that are known to absorb radiation also in the erythromogenic regions.

It is therefore an object of the present invention to provide new and useful light absorbing compositions. It is also an object of this invention to provide new and useful intermediate-range sunscreen agents, as above described, for topical use in the field of dermatology. It is a further object of this invention to provide compositions which can be applied topically to human skin and which are useful as intermediate-range sunscreen compositions.

The instant invention is directed to certain new 4-(disubstituted)aminoacylphenones and to the use of these compounds as intermediate-range sunscreen agents. Another aspect of the invention is compositions comprising such compounds formulated in a suitable acceptable pharmaceutical preparation for topical application, said sunscreen agents being used in a concentration range from about 1% to about 10%.

The instant invention more particularly describes 4-N,N-bis(w-hydroxyalkyl)-aminoacylphenones as intermediate-range sunscreen agents being employed topically in a suitable formulation at concentrations of about 1.5% to about 6%.

A preferred embodiment of particular interest to the instant invention are certain 4-N,N-bis(w-hydroxyalkyl)aminoacylphenones as intermediate-range sunscreen agents being employed at concentrations of about 1% to about 10% in a suitably acceptable pharmaceutical preparation and being the formula:

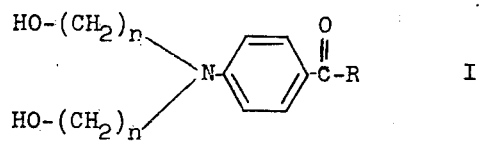

in which n is one to three and in which the acyl group

is attached to the 4 or para position of the dialkylaniline, and consists of from 2 to 16 carbon atoms, such alkyl groups, being derived from an alkanoic acid.

Another embodiment of the present invention is the use of the disclosed compounds as intermediate-range sunscreen agents for topical application, such compounds being formulated in a suitable composition at concentrations of about 1.5% to about 6%. Preferred acyl groups are those derived from the lower alkanoic acids, excluding formic acid, where R of structure I is lower alkyl, i.e., alkyl of 1 to 6 carbon chain length. Illustrative compounds suitable for use as intermediate-range sunscreen agents include 4-N,N-bis(2-hydroxyethyl)aminoacetophenone,
4-N,N-bis(2-hydroxyethyl)aminopropiophenone,
4-N,N-bis(2-hydroxyethyl)aminobutyraphenone, 4-N,N-bis(2-hydroxyethyl)aminovalerophenone, and the like.

These compounds can be formulated into well-known cosmetically and dermatologically acceptable formulations such as those hereinafter described and illustrated. In general, the formulation does not influence the actual radiation absorbing ability of the sunscreen agent, but merely facilitates the application and use thereof.

In other aspects this invention is directed to the use of the compounds of formula I in methods for the protection of various materials and substances from the effects of ultraviolet radiation. It is well-known that various pigments, plastics and other substances are deleteriously effected by ultraviolet radiation. Such materials can be conveniently protected by providing an effective amount of a suitable radiation absorbing compound either as a film on the surface of the object or as an ingredient therein. The use of light stabilizers in plastics and paints is a well-known technique. Similarly the disclosed compounds can be used in a method for preventing a particular effect of ultraviolet radiation on the skin, i.e., the skin reddening effect known as erythema. This is accomplished by providing a protective layer comprising an effective amount of a radiation screening compound. The term effective amount refers to an amount sufficient to screen out or absorb substantially all of the radiation having a wave length between about 297 nm and 320 nm. This amount will usually depend on both the absorption spectrum and the efficiency with which the radiation is absorbed, e.g., the extinction coefficient of the compound. Accordingly, the quantitative value of an effective amount will vary from compound to compound and also for differing sources of radiation.

The following examples illustrate the preparation of the compounds and formulations comprising the compounds.

EXAMPLE 1

4-N,N-bis(2-Hydroxyethyl)aminoacetophenone

A mixture of 113.5 g. (0.84 moles) of 4-aminoacetophenone 230 ml. of 2N acetic acid, and 230 ml. of ethylene oxide was heated at 130° (for 17 hours in a Parr stainless steel pressure reaction vessel). The apparatus and the reaction products were cooled and thick brown oil which solidified was obtained. The solid reaction product was broken up and enough water was added to make it filterable. After filtering and washing, the residue solid was extracted into 2.5 liters of hot methylene chloride and the hot organic phase was dried over magnesium sulfate. Upon cooling the dry methylene chloride solution, yellow crystals were formed and collected. The crystals were washed with methylene chloride and dried. Recrystallization from methylene chloride gave 58.0 g. (31.0% yield) of product as shiney yellow plates, mp. 103.5°–105.5°.

EtOH
$\lambda$ max (n.m.) = 334

(Am = 29,650). Anal.: Calc'd for $C_{12}H_{17}NO_3$: C, 64.55; H, 7.67; N, 6.27; O, 21.50. Found: C, 64.73; H, 7.59; N, 6.19.

EXAMPLE 2

4-N,N-bis(2-Hydroxyethyl)aminopropiophenone

A mixture of 125.0 gm. (0.84 mole) of 4-aminopropiophenone was reacted with ethylene oxide in the presence of 2N acetic acid as described in Example 1. The thick dark reaction product solution solidified with difficulty upon cooling and scratching. After filtering and washing with water as in Example 1, a tan solid was obtained and crystallized from a large volume of water and then recrystallized twice from methyl ethyl ketone to give 55.7 g (28.0%) of the product as off-white crystals, m.p. 97°–99°.

EtOH
$\lambda$ max (n.m.) = 330

(Am = 28,000). Calc'd for $C_{13}H_{19}NO_3$: C, 65.80; H, 8.07; N, 5.90; O, 20.23. Found: C, 65.96; H, 8.15; N, 5.85.

EXAMPLE 3

4-N,N-bis(2-Hydroxyethyl)aminobutyrophenone

4-Aminobutyrophenone (138.5 g., 0.84 mole) was reacted as described in Example 1. The brown oil reaction product was distilled in vacuo to a head temperature of 247° at 0.7 mm pressure. The distillate was discarded and the distillant solidified upon standing. The resulting crude solid was twice crystallized from methyl ethyl ketone to give 63.8 g. (30.3%) of product, mp. 70°–72°.

EtOH
$\lambda$ max (n.m.) = 332

(Am = 29,500). Anal. Calc'd for $C_{14}H_{21}NO_3$: C, 66.91; H, 8.42; N, 5.57; O, 19.10. Found: C, 66.76; H, 8.18; N, 5.53.

EXAMPLE 4

4-N,N-bis(2-Hydroxyethyl)aminovalerophenone

A mixture of 21.7 g. (0.122 mole) of 4-aminovalerophenone (Eastman) and 44 ml. each of 2N HOAc and ethylene oxide was reacted as described in Example 1. The cooled reaction product was thick brown syrup which was diluted with 50 ml. of ethyl acetate and stored at −10° overnight. The crude product (12.7 gm., mp. 50°–55°) was crystallized from benzene to give 11.2 g. (34.5%) of the product as stout colorless prisms, mp. 66°–68°.

EtOH
$\lambda$ max (n.m.) = 333

(Am = 30,300). Anal. Calc'd for $C_{15}H_{23}NO_3$: C, 67.90; H, 8.74; N, 5.28; O, 18.09. Found: C, 68.15; H, 8.73; N, 5.17.

Toxicity studies on the several 4-N,N-bis(2-Hydroxyethyl)aminoacylphenones were carried out in mice. When groups of mice were dosed daily at the level of 200 mg/kg, subcutaneously, the results during a twenty-one day test period were as follows:

| Compound | Results (deaths/subjects) |
| --- | --- |
| 4-N,N-bis(2-hydroxyethyl)aminoacetophenone | 1/5 |
| 4-N,N-bis(2-hydroxyethyl)aminopropiophenone | 0/5 |
| 4-N,N-bis(2-hydroxyethyl)aminobutyrophenone | 0/5 |
| 4-N,N-bis(2-hydroxyethyl)aminovalerophenone | 0/5 |

When groups of five mice each were dosed orally with the compounds in acacia suspension at the levels of 200 mg/kg and 500 mg/kg per day during a twenty-one day test period, the results were as follows:

| Compound | 200 mg/kg (deaths/subjects) | 500 mg/kg (deaths/subjects) |
| --- | --- | --- |
| 4-N,N-bis(2-hydroxyethyl)aminoacetophenone | 1/5 | 1/5 |
| 4-N,N-bis(2-hydroxyethyl)aminopropiophenone | 1/5 | 5/5 |
| 4-N,N-bis(2-hydroxyethyl)aminobutyrophenone | 0/5 | 0/5 |
| 4-N,N-bis(2-hydroxyethyl)aminovalerophenone | 0/5 | 0/5 |

From the above toxicity data, it is apparent that these 4-N,N-bis(2-hydroxyethyl)-aminoacylphenones are relatively non-toxic.

Irritation tests were carried out by occluding the compound being tested on freshly shaved rabbit skin under a one centimeter square gauze patch upon which there had been placed 0.5 c.c. of a 5% solution of the particular compound dissolved in a 60–40 ethanol-water mixture. Occlusion was maintained for twenty-four hours after which the test area was evaluated for irritation as evidenced by edema or erythema. The rating scale was 0–4 for both edema and erythema. The results of the tests were as follows:

| Compound | Edema | Erythema |
| --- | --- | --- |
| 4-N,N-bis(2-hydroxyethyl)aminoacetophenone | 0 | 0 |
| 4-N,N-bis(2-hydroxyethyl)aminopropiophenone | 0 | 0 |
| 4-N,N-bis(2-hydroxyethyl)aminobutyrophenone | 0 | 0 |
| 4-N,N-bis(2-hydroxyethyl)aminovalerophenone | 0 | 0 |

It can be seen from the above test results that these 4N,N-bis(2-hydroxyethyl)-aminoacylphenones are not irritating.

The 4-N,N-bis(2-hydroxyethyl)aminoacylphenones were formulated into sunscreen preparations to give preparations of several types. Representative formulations are as follows:

Formulation No. 1 — The following formulation provides a cosmetically acceptable lotion-type sunscreen preparation:

| % | Component |
| --- | --- |
| 2.0000 | Polyoxyethyleneglycol - 200 dilaurate |
| 1.0000 | Polyoxyethylene lauryl ether |
| 0.5833 | Dewaxed fraction of lanolin |
| 15.9167 | Mineral oil |
| 5.0000 | Glyceryl monostearate |
| 5.0000 | Polyoxol - 40 stearate |
| 0.1042 | Sodium dioctylsulfosuccinate, 75% |
| 59.4167 | Deionized water |
| 0.1771 | Carboxyvinyl polymers |
| 0.2500 | Methyl paraben |
| 5.0000 | 4-N,N-bis(2-Hydroxyethyl)aminoacetophenone |
| 5.0000 | Propylene glycol |
| 0.1354 | Triethanolamine |
| 0.2083 | PA-1614 Perfume |
| 0.2083 | Propyl paraben |
| 100.0000 | |

Formulation No. 2 — The following formulation provides a cosmetically acceptable lotion-type sunscreen preparation:

| % | Component |
| --- | --- |
| 5.0000 | Polyoxol - 40 stearate |
| 0.1042 | Sodium dioctylsulfosuccinate, 75% |
| 0.2083 | Propyl paraben |
| 61.9167 | Deionized water |
| 0.1771 | Carboxyvinyl polymers |
| 0.2500 | Methyl paraben |
| 5.0000 | Propylene glycol |
| 2.5000 | 4-N,N-bis(2-hydroxyethyl)aminoacetophenone |
| 0.1354 | Triethanolamine |
| 0.2083 | PA-1614 Perfume |
| 2.0000 | Polyethyleneglycol - 200 dilaurate |
| 1.0000 | Polyoxyethylene lauryl ether |
| 0.5833 | Dewaxed fraction of lanolin |
| 15.9167 | Mineral oil |
| 5.0000 | Glyceryl monostearate |
| 100.0000 | |

Formulation No. 3 — The following information provides a cosmetically acceptable hydro-alcoholic liquid sunscreen preparation:

| % | Component |
| --- | --- |
| 32.86 | Demineralized Water |
| 0.14 | Hydroxymethylcellulose |
| 55.00 | SDA-40 |
| 2.00 | Ethoxylated cholesterol derivatives |
| 5.00 | Glycerin USP |
| 5.00 | 4-N,N-bis(2-Hydroxyethyl)aminoacetophenone |

Formulation No. 4 — The following formulation provides a cosmetically acceptable clear gel as a sunscreen preparation:

| % | Component |
| --- | --- |
| 4.000 | Polyoxyethylene (4) lauryl ether |
| 0.072 | Lemon Chantia 46136F |
| 60.000 | SDA-40 |
| 27.328 | Demineralized Water |
| 2.000 | Carboxyvinyl polymer |
| 0.050 | 1% D & C Yellow No. 10 solution |
| 0.050 | 1% FD & C Brille Blue No. 1 solution |
| 0.500 | Ethoxylated propoxylpropylene glycol |
| 5.000 | 4-N,N-bis(2-hydroxyethyl)aminoacetophenone |
| 1.000 | Diisopropylamine |
| 100.000 | |

Formulation No. 5 — The following formulation provides a cosmetically acceptable clear gel as a sunscreen preparation:

| % | Component |
|---|---|
| 60.000 | SDA 40 |
| 4.000 | Polyoxyethylene (4) lauryl ether |
| 2.000 | Carboxyvinyl polymer |
| 0.072 | Lemon Chantia 46136F |
| 0.050 | 1% D & C Yellow No. 10 solution |
| 0.050 | 1% FD & C Brille Blue No. 1 solution |
| 29.828 | Demineralized Water |
| 2.500 | 4-N,N-bis(2-Hydroxyethyl)aminoacetophenone |
| 0.500 | Ethoxylated propoxylpropylene glycol |
| 1.000 | Diisopropanolamine |
| 100.000 | |

Formulation No. 6 — The following formulation provides a cosmetically acceptable sunscreen composition as an emulsion-type cream:

| % | Component |
|---|---|
| 38.60 | Demineralized Water |
| 0.10 | Methyl paraben |
| 5.00 | Propylene glycol |
| 5.00 | 4-N,N-bis(2-Hydroxyethyl)aminoacetophenone |
| Q.S. | 1% Yellow No. 10 solution |
| Q.S. | 1% FD & C Brille Blue solution |
| 16.00 | Mineral Oil, U.S.P. |
| 3.00 | Ceresin Wax |
| 3.00 | Lanolin - derived sterol and alcohol extracts |
| 0.10 | Propyl paraben |
| 2.00 | Glyceryl monostearate |
| 5.00 | 70% water solution of sorbitol |
| 2.00 | Magnesium stearate |
| 10.00 | No. 5211 Talc |
| 10.00 | Urea |
| 0.10 | Perfume No. 9151 |
| 0.10 | Perfume No. 80533 |
| 100.00 | |

The above described formulations illustrate the general compositions of various types. Any of the herein disclosed compounds can be incorporated into the various types of formulations.

What is claimed is:

1. A method for protecting human skin from the erythemic effect of ultraviolet radiation which comprises applying to the skin a compound having the formula

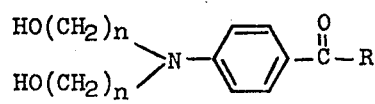

wherein $n$ is an integer of from 1 to 3 and R is an alkyl group having from 2 to 16 carbon atoms, said compound being applied in an amount sufficient to screen out substantially all of the radiation having a wave length between about 297nm and 320nm.

2. The method of claim 1 wherein $n$ is 2.

3. The method of claim 1 wherein R is an alkyl group containing from 1 to 6 carbon atoms.

4. The method of claim 1 wherein the compound has the formula

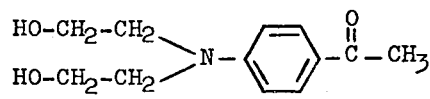

5. The method of claim 1 wherein the compound has the formula

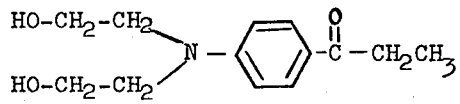

6. The method of claim 1 wherein the compound has the formula

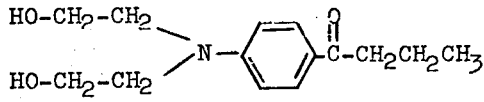

7. The method of claim 1 wherein the compound has the formula

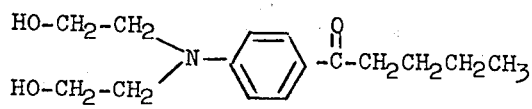

* * * * *